United States Patent
Medici

(10) Patent No.: US 8,721,985 B2
(45) Date of Patent: May 13, 2014

(54) DEVICE AND METHOD FOR TREATING AND ANALYSING CHANNELS IN INSTRUMENTS, PARTICULARLY IN ENDOSCOPES

(75) Inventor: Antonio Medici, Hochdorf (CH)

(73) Assignee: Belimed AG, Zug (CH)

( * ) Notice: Subject to any disclaimer, the term of this patent is extended or adjusted under 35 U.S.C. 154(b) by 93 days.

(21) Appl. No.: 12/761,890

(22) Filed: Apr. 16, 2010

(65) Prior Publication Data

US 2010/0266447 A1   Oct. 21, 2010

(30) Foreign Application Priority Data

Apr. 20, 2009 (EP) .................................. 09158261

(51) Int. Cl.
*A61L 2/00* (2006.01)
*B08B 3/00* (2006.01)
*A61B 1/00* (2006.01)

(52) U.S. Cl.
USPC ........... 422/297; 422/292; 422/300; 422/301; 134/94.1; 600/133

(58) Field of Classification Search
USPC ............. 422/292, 297, 300, 301, 28, 32, 105, 422/119; 134/8, 14, 22.1, 22.18, 56 R, 94.1; 600/101, 133; 73/1.02, 1.16, 37
See application file for complete search history.

(56) References Cited

U.S. PATENT DOCUMENTS

| | | | |
|---|---|---|---|
| 5,279,799 A | 1/1994 | Moser | |
| 6,606,573 B2 * | 8/2003 | Wheeler | ...................... 702/56 |
| 2004/0134520 A1 * | 7/2004 | Weber | .................... 134/22.12 |
| 2005/0209507 A1 | 9/2005 | Suzuki et al. | |

FOREIGN PATENT DOCUMENTS

| | | |
|---|---|---|
| DE | 43 14 364 A1 | 11/1993 |
| DE | 102 08 035 A1 | 9/2003 |
| DE | 103 52 198 A1 | 6/2005 |
| EP | 0 483 059 A1 | 4/1992 |
| EP | 1 319 411 A1 | 6/2003 |

(Continued)

OTHER PUBLICATIONS

European Patent Office Translation of the Description section of DE 43 14 364 (Nov. 1993).*

(Continued)

*Primary Examiner* — Monzer R Chorbaji
(74) *Attorney, Agent, or Firm* — Nath, Goldberg & Meyer; Jerald L. Meyer; Sanjana Mangalagiri

(57) ABSTRACT

The device is suitable in particular for treating medical endoscopes. At least one treatment fluid is fed through a conduit system (3) to a channel attachment (4), to which a channel of the instrument to be treated can be attached. The conduit system has a fluid attachment (39), which can be connected to a source of treatment fluid. With the aid of a measuring device, the flow of the treatment fluid in the conduit system, and thus the permeability of the attached channel, can be measured. The measurement is effected with the aid of a measurement section (6) in which a flow sensor (7, 7') is arranged. All the treatment steps are carried out via the conduit system and in particular also via the measurement section. In this way, the conduit system is subjected to the same process as the instrument to be treated, and a flow measurement can be carried out in each individual treatment step.

10 Claims, 13 Drawing Sheets

(56) References Cited

FOREIGN PATENT DOCUMENTS

Figure 1:
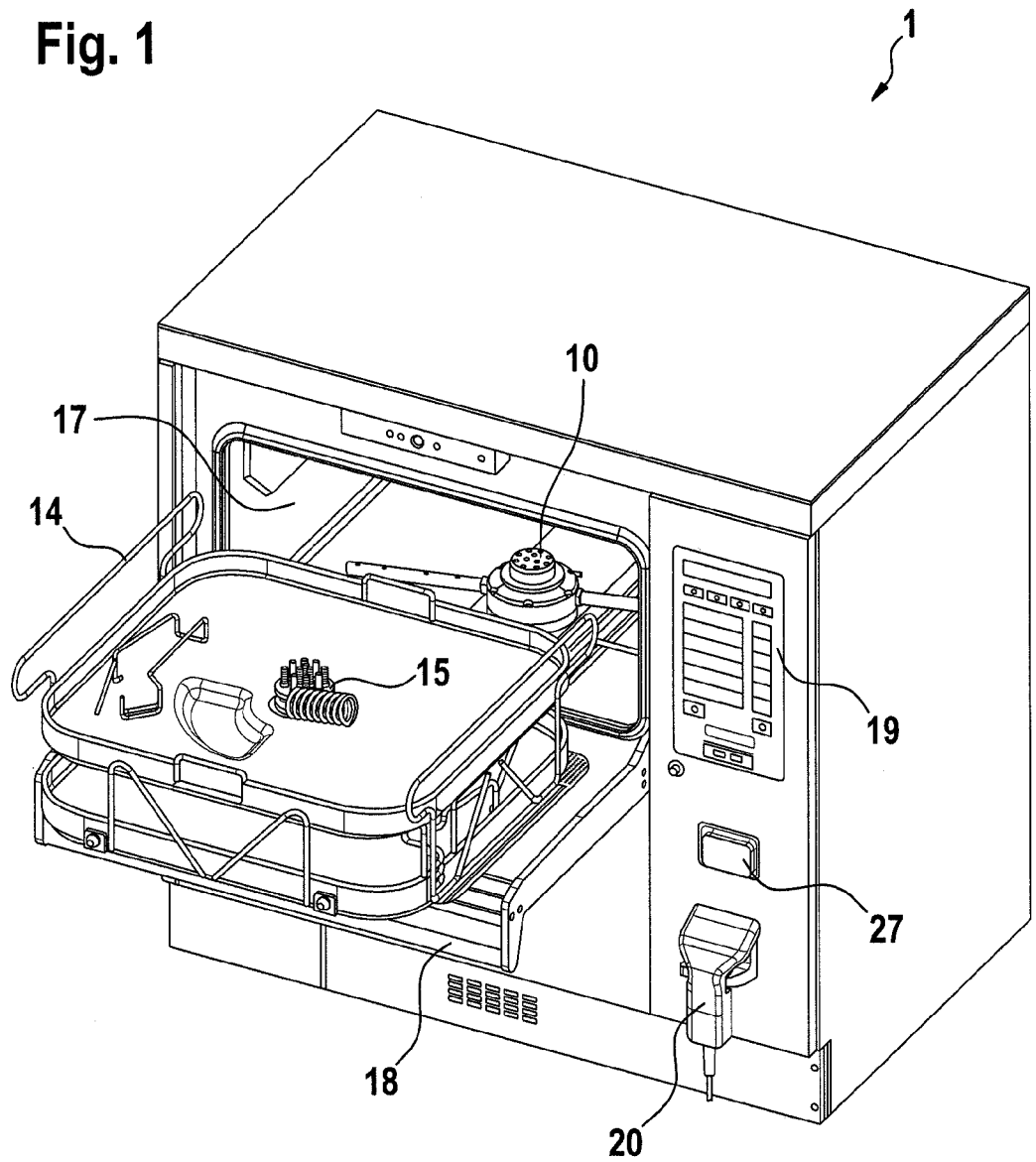

| | | | | |
|---|---|---|---|---|
| EP | 1 502 538 A1 | 2/2005 | | |
| JP | 43 14 364 | * 11/1993 | ................ | G01F 1/68 |
| JP | 2001-299697 A | 10/2001 | | |

OTHER PUBLICATIONS

"Fehlertolerantes Regelsystem", Wikipedia, last visited Jul. 30, 2013, four (4) pages, with English Abstract.

Vetter, "Vorwort", Handbuch Dosieren, (1994), ISBN 3-8027-2167-5, seven (7) pages, with English Abstract.

* cited by examiner

DEVICE AND METHOD FOR TREATING AND ANALYSING CHANNELS IN INSTRUMENTS, PARTICULARLY IN ENDOSCOPES

The invention relates to a device and a method for treating and analysing channels in instruments, particularly in endoscopes. This concerns machine treatment of instruments, which can be endoscopes used in human medicine or in veterinary medicine, but also in individual cases other instruments for industrial or scientific purposes, with channels that have to be cleaned after a certain period of use of the instrument. In the case of endoscopes, the treatment process is usually understood as a process that comprises a sequence of rinsing, cleaning, disinfecting and drying. To ensure that no contaminants have been left behind in the channels, the state of the channels has to be analysed during the treatment process, with the permeability of the channels forming a measure of their cleanliness.

Many comparable methods and devices of these kinds are already known. According to DE 103 52 198, a defined volume of a treatment liquid is forced with a predetermined pressure through an endoscope channel, with the period of time needed for this process being measured. JP 2001 299 697 describes a device for washing and disinfecting endoscopes, in which the through-flow rate in each of the respective endoscope channels can be determined, and in which a flow sensor is used. A further device for cleaning and testing endoscopes is described in U.S. Pat. No. 5,279,799.

A problem with the known methods and devices is in particular that residues from a preceding process step can be carried over into the next process step, such that, for example, cleaning agent gets into the next disinfecting process. This problem arises from the fact that, in the known devices, the conduit system is composed of flexible tubes in which pockets can form that can no longer be emptied after completion of a process step. Further disadvantages of the known systems are that the sometimes different and/or branched channels of an endoscope cannot be treated individually and also cannot be analysed individually. A shortcoming of the known prior art is in some cases also the actual measurement methods, which react only to certain treatment fluids. Finally, a leak in the system may go unnoticed, with the result that not enough treatment fluid reaches the instrument.

It is therefore an object of the invention to make available a device of the type mentioned at the outset, with the aid of which the instruments can be treated and analysed in an absolutely reliable and automated manner. In particular, treatment agents are to be prevented from being carried over from one process step to a subsequent process step. Moreover, the flow measurement should take place in a reliable manner and under the same operating conditions at all times. The device should also permit the treatment and analysis of the greatest possible number of individual channels in the same process.

The conduit system has a measurement section, and the measuring device has at least one flow sensor arranged in the measurement section. All the treatment steps can be executed via the conduit system and in particular via the measurement section with the flow sensor. This has the great advantage that the through-flow of all the treatment fluids can be measured, regardless of whether they are liquid or gaseous, and regardless of the sequence, and in addition that the entire conduit system and the sensors can be subjected to the same processes as the instrument itself. The fluid attachment can be connected to at least one source of treatment fluid, and a delivery means is preferably present for conveying the treatment fluid through the conduit system and through the attached channel.

The delivery means can be a pump, for example. However, another pressure source is also conceivable, such as a tank under air pressure, etc.

The flow is advantageously measured on a measurement section that extends directly below the plane on which the channel attachment lies, wherein the entire conduit system, and in particular the measurement section, is inclined with respect to the horizontal plane and is oriented preferably perpendicular thereto. By virtue of the ascending arrangement of the conduit system, it can be completely emptied of treatment liquid without pockets with residues being able to form. The emptying can take place simply by gravity, with the delivery means deactivated. Alternatively, however, aspiration is also possible.

The flow sensor is particularly advantageously a thermoelectric sensor, which determines the flow without movable parts. Thermoelectric flow sensors are known per se and customary. A thermal flow sensor is described in DE 43 13 364, for example. The measurement principle is based on the fact that the fluid flowing through causes cooling, and a constant temperature is maintained with the aid of a heating element. The current delivered to the heating element is a measure of the through-flow of the fluid.

Two flow sensors, with which the flow can be measured redundantly, are particularly advantageously arranged one after the other in the measurement section. A particularly high degree of reliability is thus achieved, since the sensors are also controlled during the process. If the two sensors measure unequal values, this may point to a defect on one of the sensors.

An inlet valve is advantageously arranged between the flow sensor and the channel attachment, which inlet valve shuts off the entire conduit system from the outside before the start of the treatment process. This shut-off is provided for safety reasons and in order to prevent back-contamination of the conduit system.

Further advantages can be achieved if several conduit systems are combined to form a measuring unit, wherein each conduit system leads to a conduit attachment, and wherein all the conduit attachments are arranged on a common attachment head. In this way, multi-channel instruments and/or several instruments at the same time can be treated, with each individual channel having an autonomous measurement system. All the conduit attachments are combined on the attachment head, which makes handling considerably easier and which is also advantageous for reasons of space.

All the conduit systems can be fed with the treatment fluid via a common distributor chamber. In the case of identically designed conduit systems, the same operating pressure thus prevails in each conduit system. The common distributor chamber also facilitates the simultaneous and rapid emptying of the conduit system and the change from one treatment fluid to the next.

For construction reasons, it is particularly advantageous if all the conduit systems, preferably at least four, are arranged preferably in a circle shape or star shape around a central, preferably vertical axis. In a particularly advantageous arrangement, eight conduit systems are arranged in a circle. In this arrangement, the flow sensors and any other components, e.g. electronic parts, valves, etc., are easily accessible from the outside.

In the described arrangement of the conduit systems, the abovementioned attachment head can be lifted away from the measuring unit, by means of a lifting device, from a rest position to a preferably higher operating position in which the conduit attachments can be docked onto an attachment adapter assigned to a receiving basket for the instruments. In this way, the receiving basket with the attachment adapter can be loaded outside the appliance or outside the treatment chamber, with the individual channels of the instrument being attached to the adapter in a prescribed order in each case. After the receiving basket has been inserted into the appliance chamber, the channels systems are attached automatically. Of course, it would be conceivable to dock only a single channel system onto an attachment adapter in exactly the same way, or to design individual groups of channel systems that can be individually docked.

The connection between the measuring unit and the attachment head is advantageously effected by riser pipes, which are movable telescopically in the measuring unit. In this way, the entire measuring unit can be mounted securely under the treatment chamber in the appliance, with only the riser pipes moving with the attachment head between the rest position and the operating position.

The conduit system preferably exclusively comprises rigid tubular conduits, in order to avoid the formation of pockets. The rigid tubular conduits also have the advantage that they cannot deform under the effect of heat or chemicals, for example, such that no unwanted change in cross section occurs. The expression tubular conduit is understood in principle as any conduit route, for example also a bore in a block of material.

In terms of method, the object is achieved with the aid of a method in which the measurement is effected by means of a flow sensor on a measurement section, and all the treatment steps are carried out via the conduit system and in particular via the measurement section with the flow sensor. In this way, it is ensured that the measurement section with the sensors is also permanently subject to the same treatment steps as the instrument to be treated. This also applies in particular to the same treatment temperature and in particular also to at least one chemical and/or thermal disinfection. The conduit system is thus permanently subject to a self-cleaning process, and the reduction in the number of microorganisms in the conduit system is the same as in the instrument to be treated.

The delivery of the treatment fluid from the bottom upwards, in relation to a horizontal plane, in the measurement section and preferably in the entire conduit system, permits a reliable measurement under what are at all times the same hydrostatic conditions and, moreover, a complete emptying of the conduit system and in particular of the measurement section.

The treatment fluid is preferably delivered at the same pressure simultaneously through several conduit systems, each of which leads to a channel attachment, and the flow is measured on each conduit system.

For precise analysis of the channels, it is also particularly advantageous if different treatment fluids are delivered one after another through the same conduit system, and if the flow of individual treatment fluids or of all the treatment fluids is measured. The thermoelectric sensors preferably used allow a flow measurement not only of any desired liquids, but also of gases. It is thus conceivable, for example, to determine the state of the channels even when drying air is being passed through them.

The flow on each measurement section is particularly advantageously measured redundantly by means of two flow sensors, with the two measurements being evaluated independently and compared to each other. A comparison device can be used that is set to a defined tolerance value, such that the process is automatically interrupted and/or a warning signal is triggered when this tolerance value is exceeded.

Figure 2:
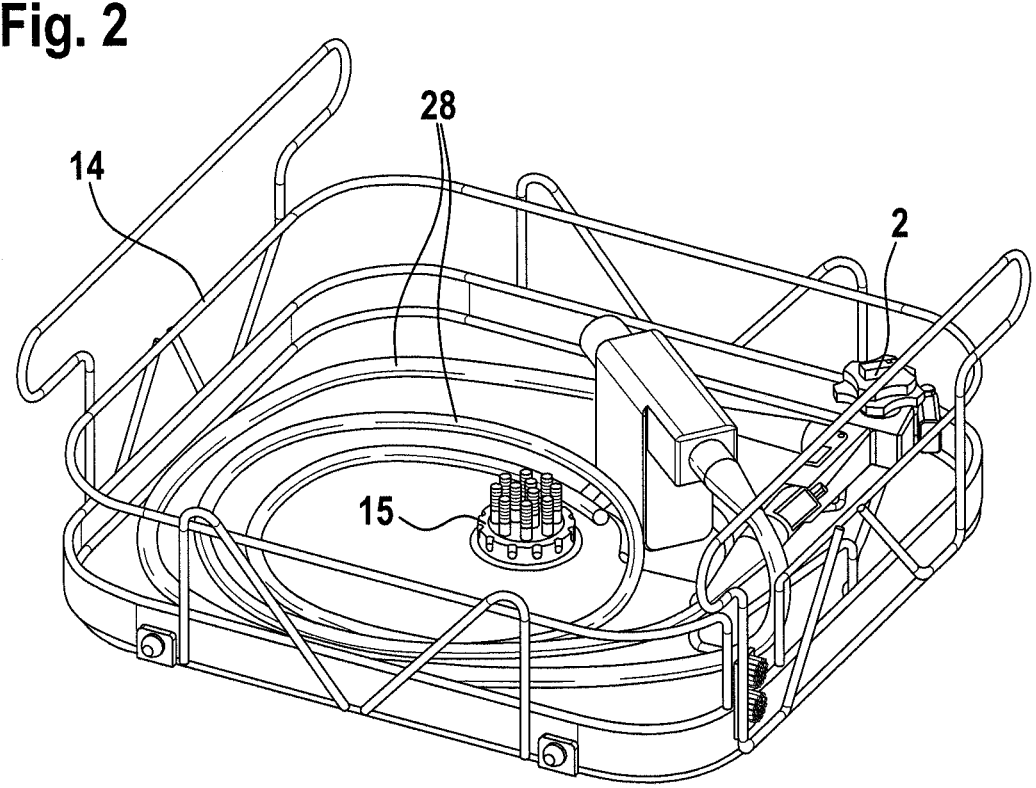
Figure 3:
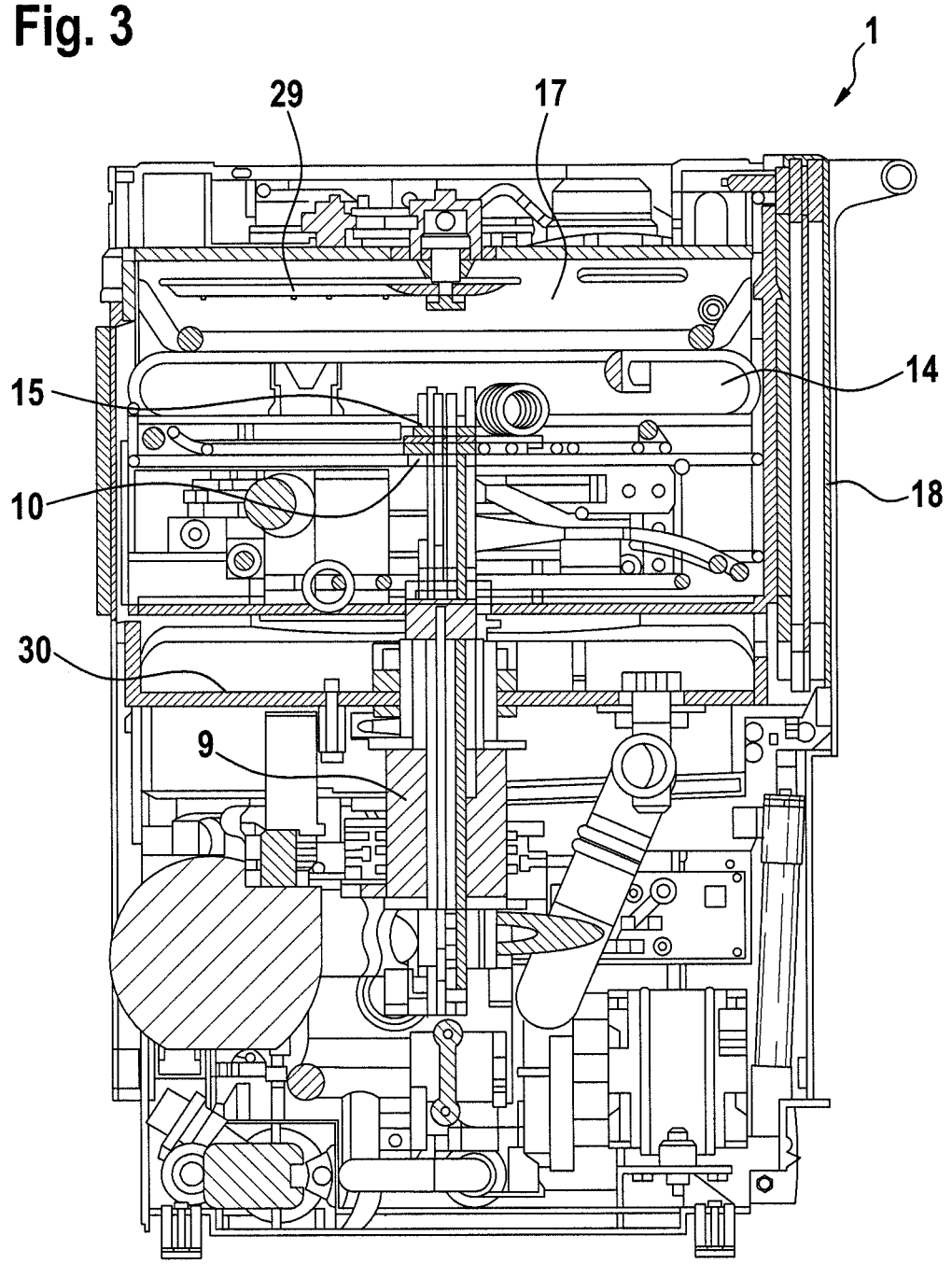
Figure 4:
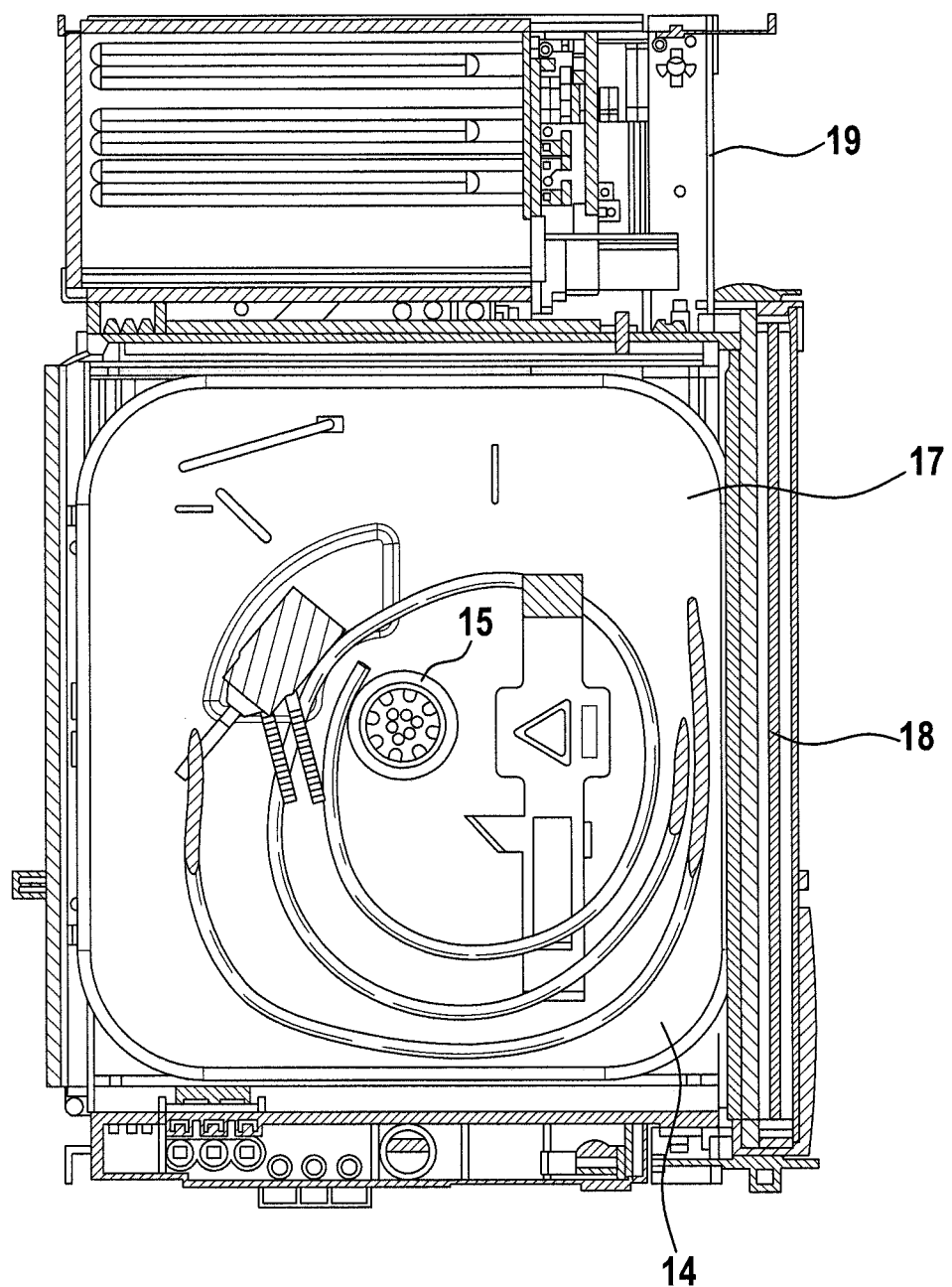
Figure 5:
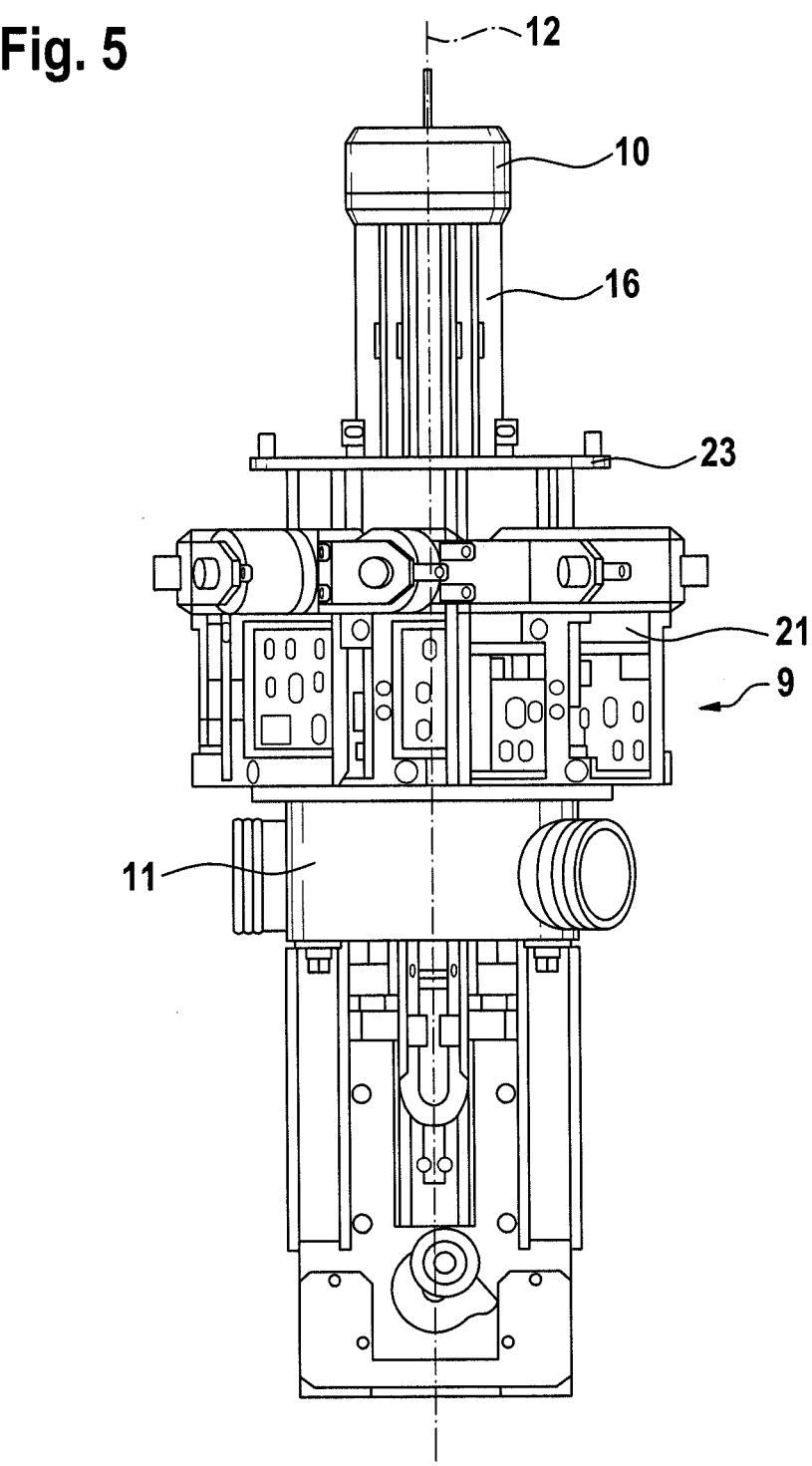
Figure 6:
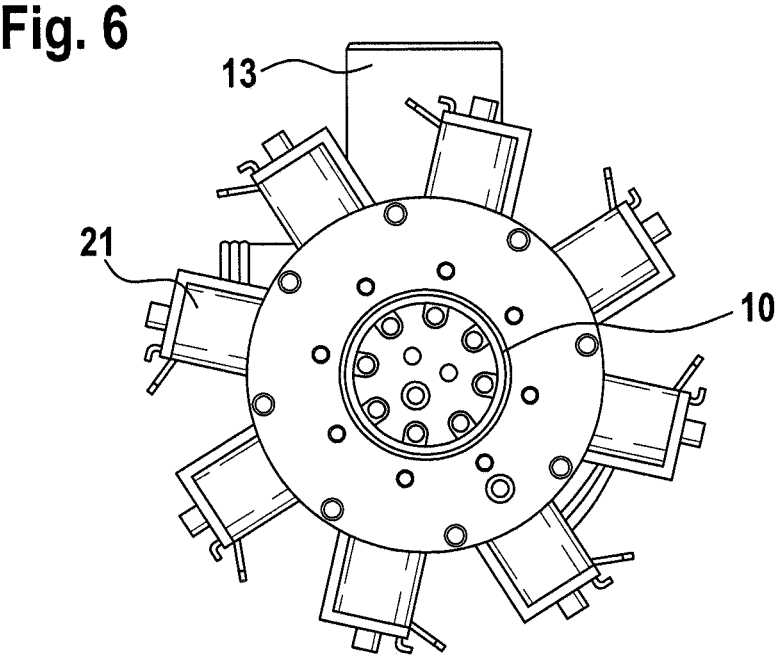
Figure 7:
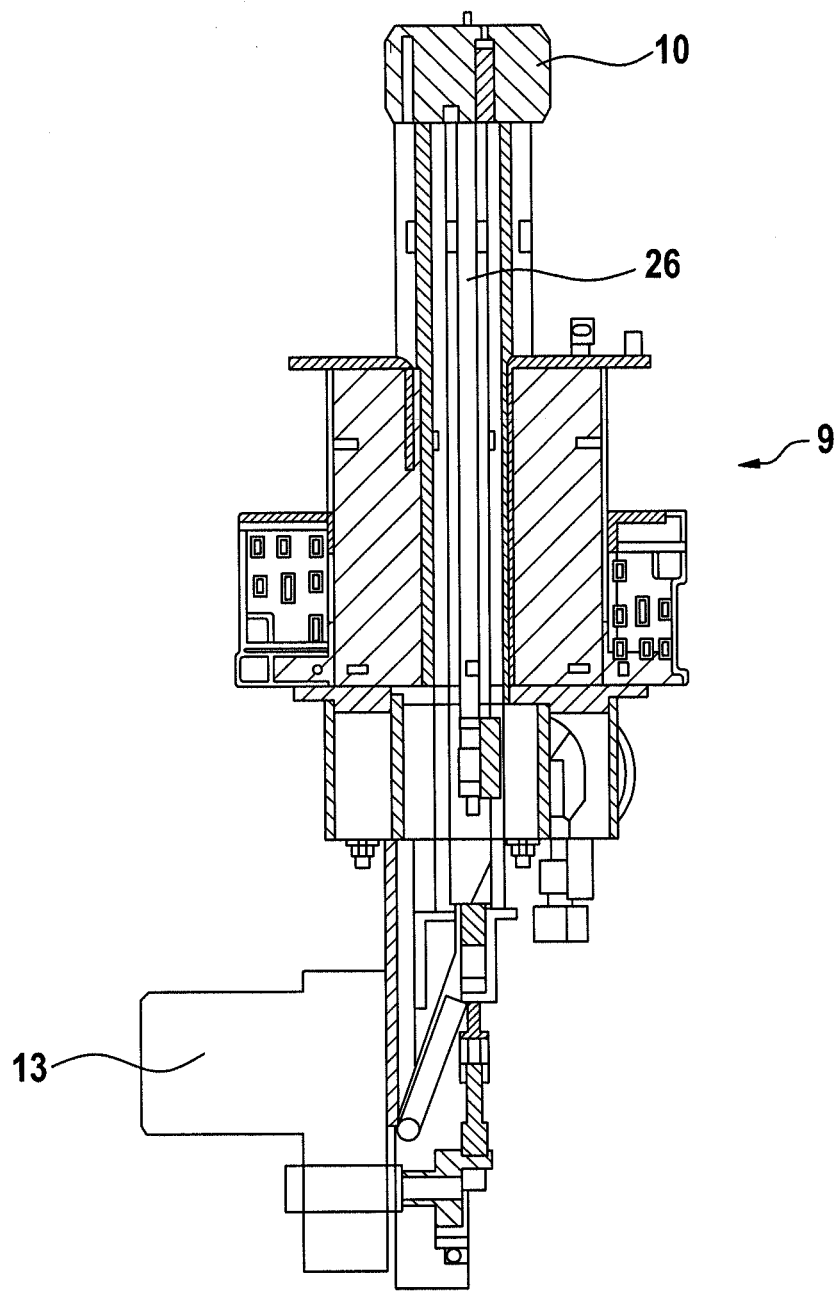
Figure 8:
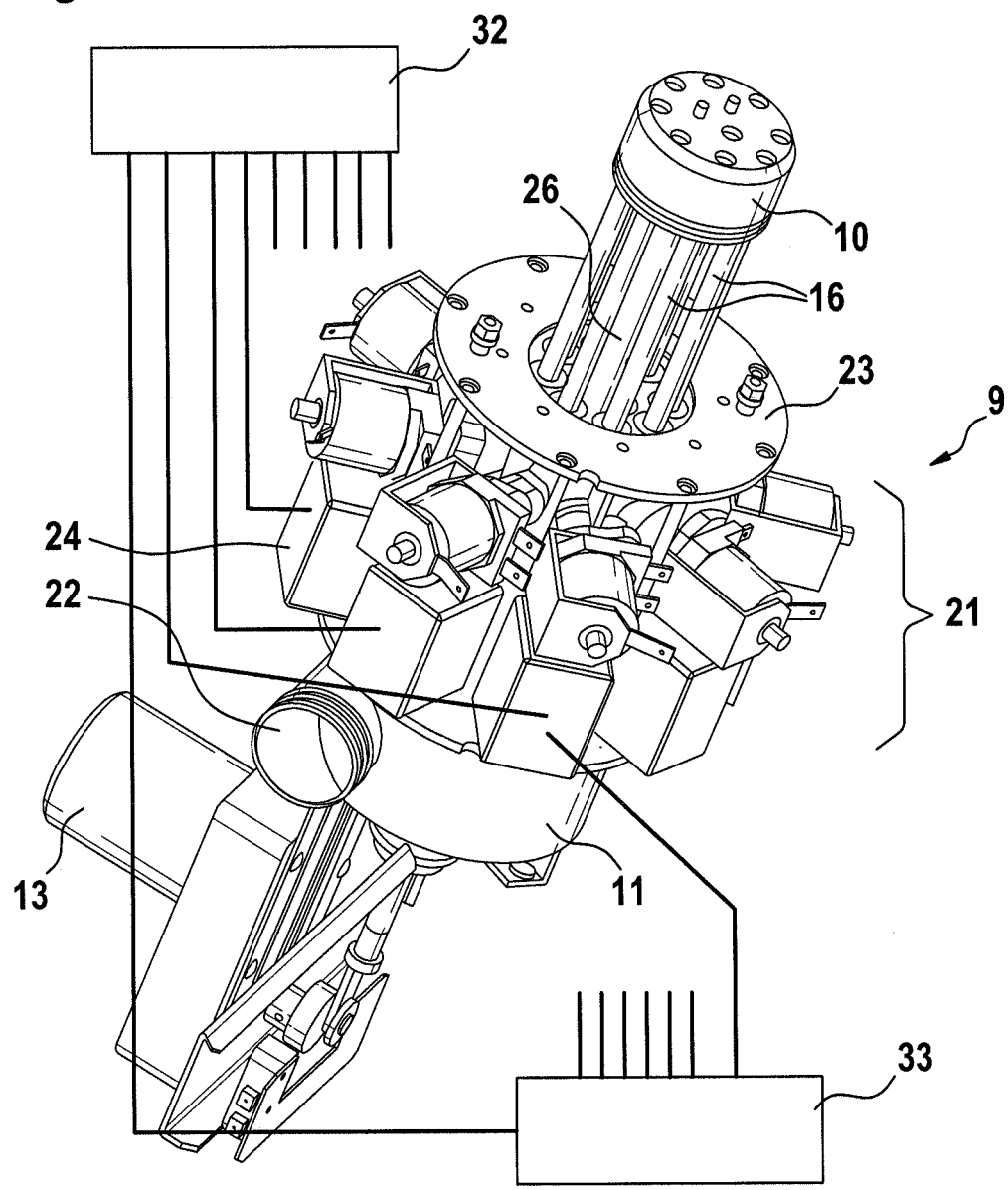
Figure 9:
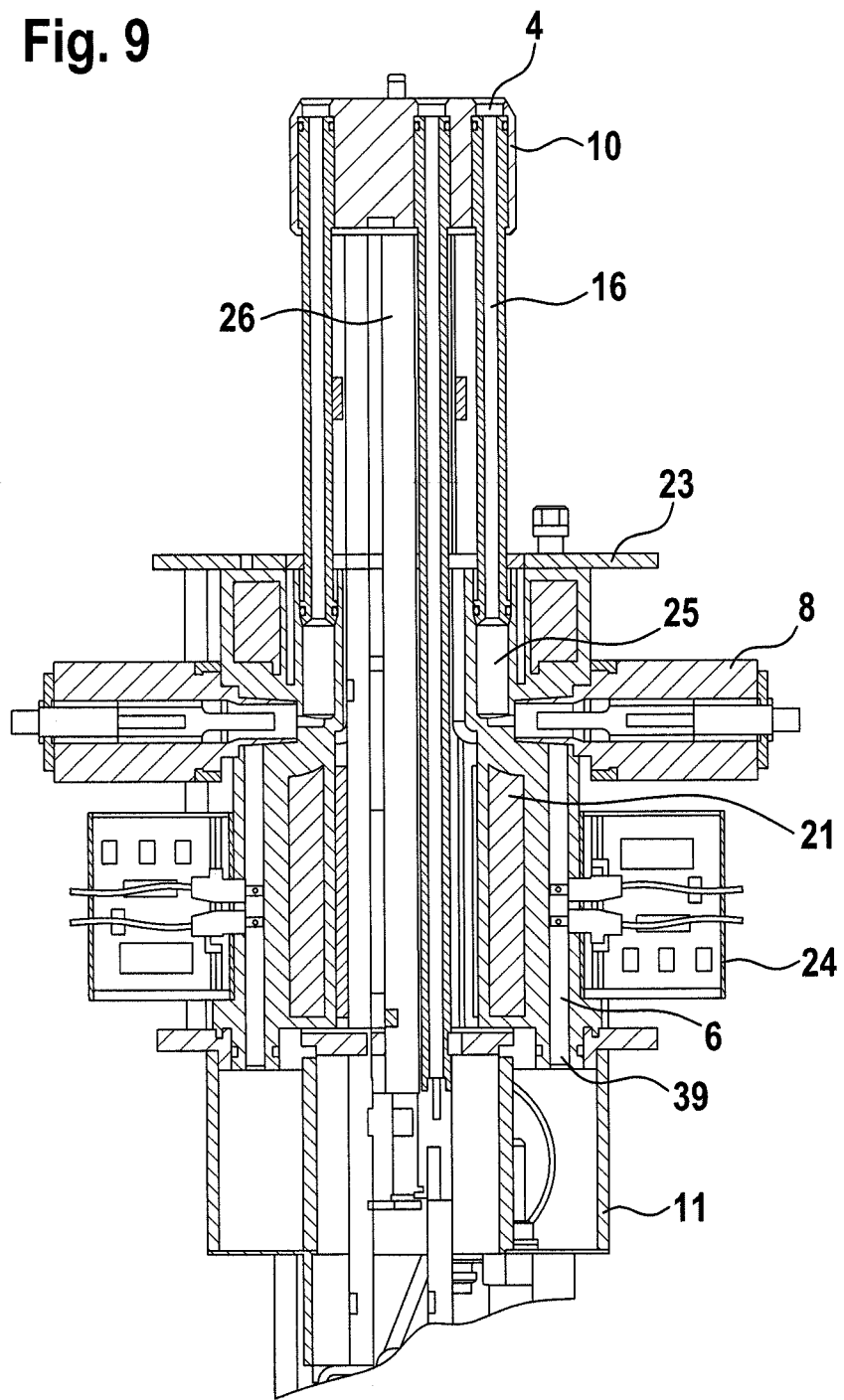
Figure 10:
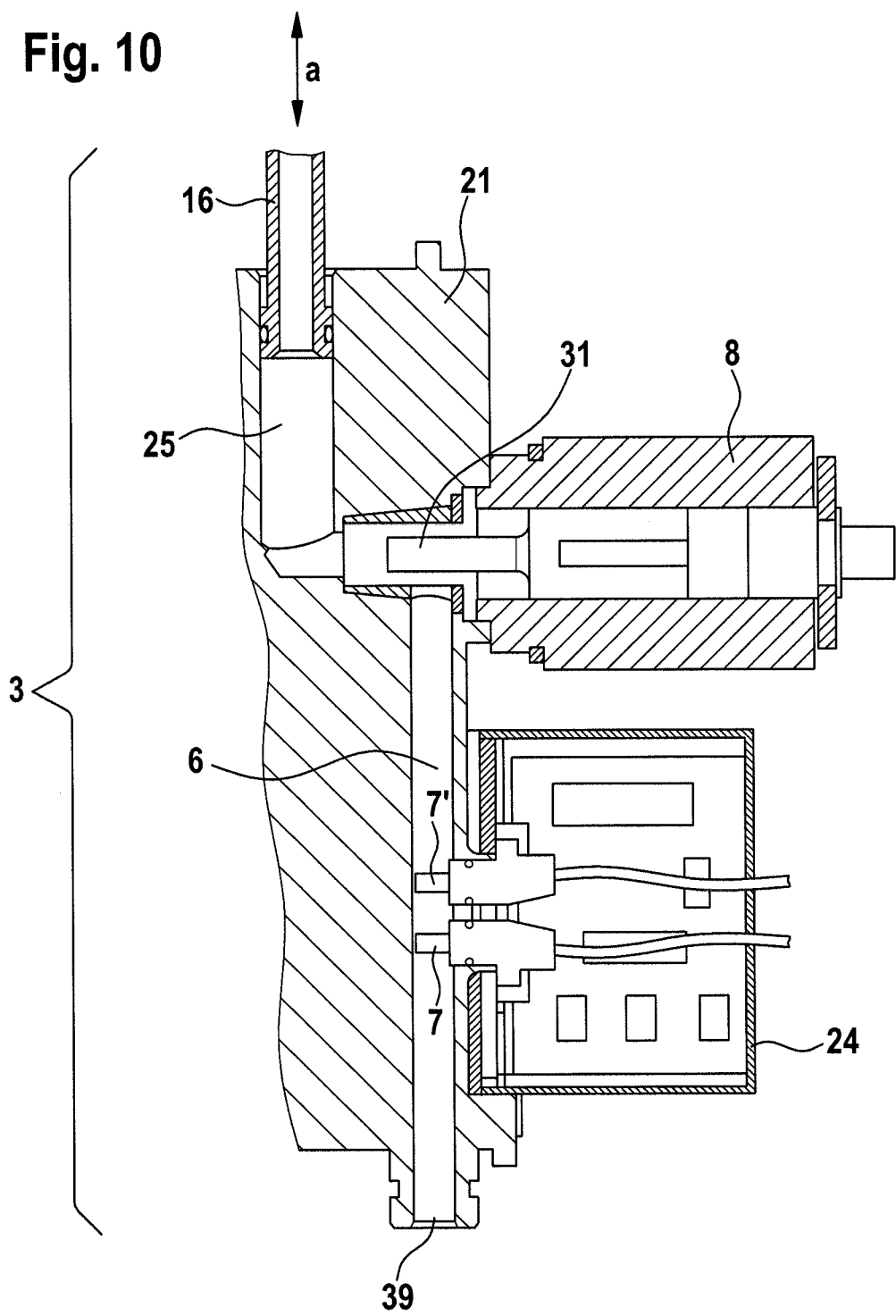
Figure 11:
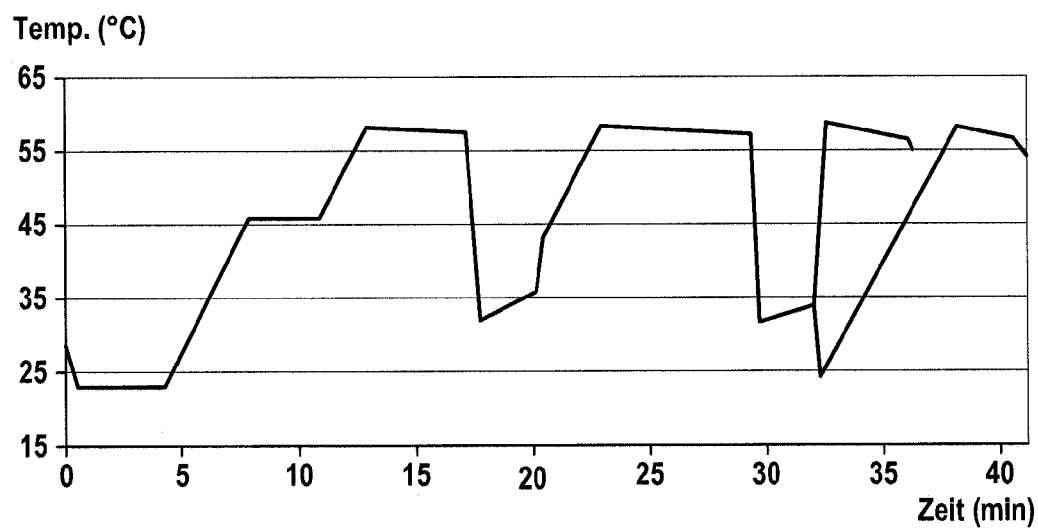
Figure 12:
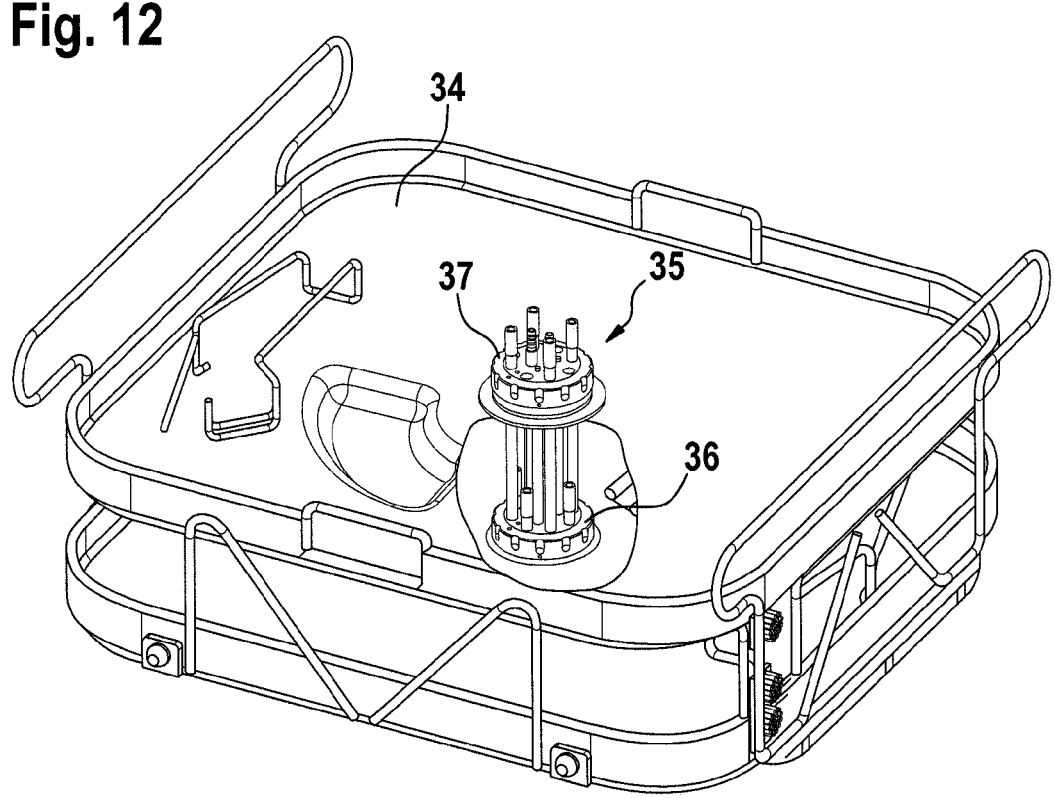
Figure 13:
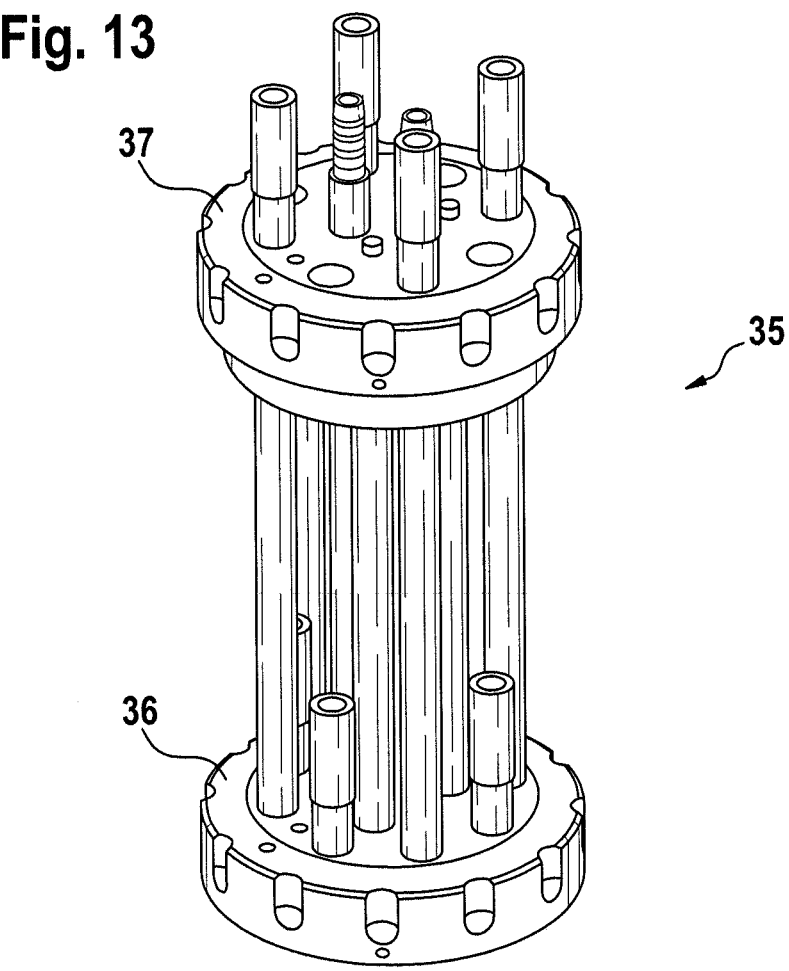
Figure 14:
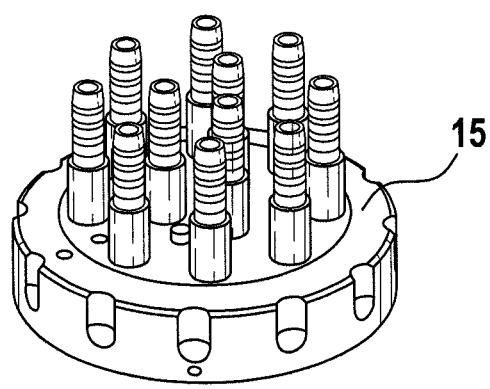
Figure 15:
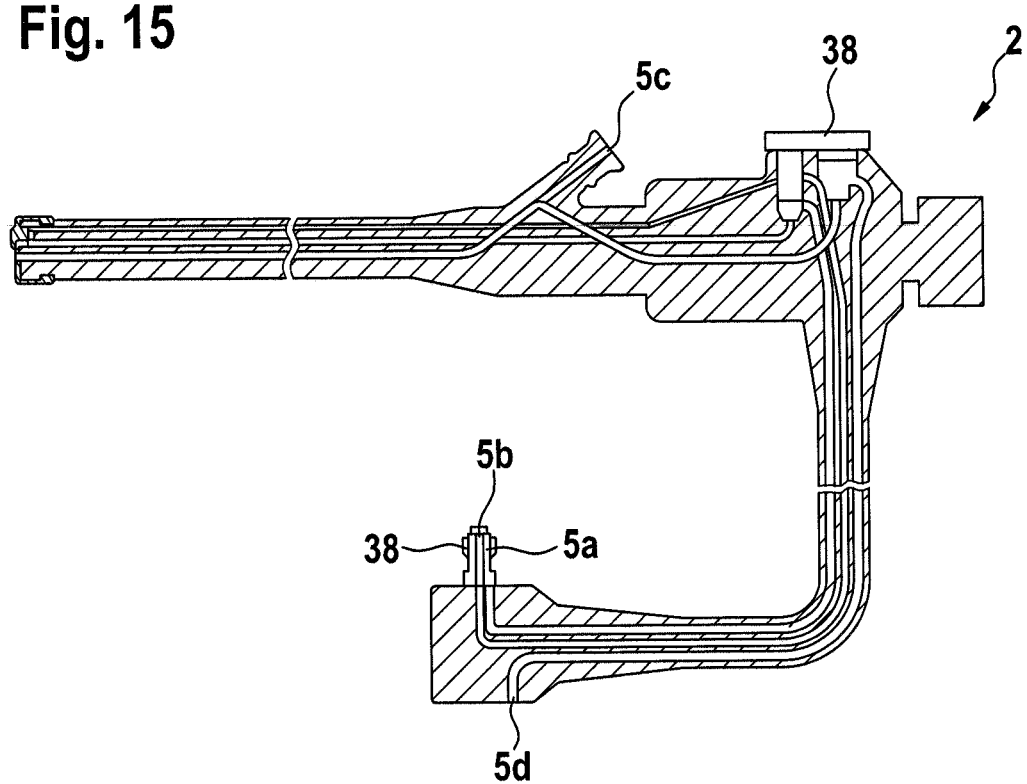

Further advantages and individual features of the invention will become clear from the following description of an illustrative embodiment and from the drawings, in which:

FIG. 1 shows a perspective view of a treatment appliance with the door opened and the receiving basket pulled out, FIG. 2 shows a perspective view of a receiving basket with an attachment adapter and with an inserted endoscope, FIG. 3 shows a vertical cross section through the appliance according to FIG. 1, FIG. 4 shows a horizontal cross section through the appliance according to FIG. 3 over the receiving basket, FIG. 5 shows a side view of the measuring unit installed in the appliance according to FIG. 3, with several channel systems, FIG. 6 shows a plan view of the measuring unit according to FIG. 5, FIG. 7 shows a vertical cross section through the measuring unit according to FIG. 5, FIG. 8 shows a perspective view of the measuring unit according to FIG. 5 obliquely from above, FIG. 9 shows a partial cross section through the measuring unit according to FIG. 8, FIG. 10 shows an enlarged cross section of an individual measurement cell of the measuring unit according to FIG. 9, FIG. 11 shows a temperature/time diagram of a treatment process with various treatment fluids, FIG. 12 shows an alternative receiving basket for the appliance according to FIG. 1, but with two receiving planes for appliances, FIG. 13 shows a perspective view of an attachment adapter for two treatment planes, FIG. 14 shows a slightly enlarged view of the attachment adapter shown in FIG. 2, and FIG. 15 shows a schematic example of an endoscope with several channels.

As is shown in FIG. 1, a treatment appliance designated generally by reference number 1 has a wash chamber 17, which can be closed by means of a wash chamber door 18. A receiving basket 14 for the endoscopes that are to be treated can be pushed into the wash chamber 17 via suitable guides. When the receiving basket 14 is pushed in and the wash chamber door 18 has been closed, an attachment head 10, still visible here at the bottom of the wash chamber, communicates with an attachment adapter 15 at the bottom of the receiving basket, in a manner that will be described below. The appliance has a control panel 19 on which the individual processes can be set and on which the respective process steps can be read off. A barcode reader 20 is also arranged on the appliance in order to be able to identify the encoded endoscopes before insertion into the wash chamber. In this way, the specific treatment steps can be assigned to each endoscope, and a printer 27 can print out a batch protocol.

FIG. 2 shows how an endoscope 2 with its hose lines is arranged in the receiving basket 14. In the illustrative embodiment, the receiving basket 14 is composed of a wire structure, although it could also have any other desired construction. The aforementioned attachment adapter 15 is arranged on the bottom of the receiving basket, but the individual hose lines 28 of the endoscope are not yet plugged onto the individual adapter attachments.

Further details of the structure of the appliance will be seen from FIGS. 3 and 4. The wash chamber door 18 is closed here, and the receiving basket 14 is pushed into its operating position. As is shown, the attachment head 10 is now located in the raised operating position, in which it is docked from below onto the attachment adapter 15 of the receiving basket 14. The attachment head 10 is a component part of a measuring unit designated overall by reference number 9, which measuring unit is arranged on the bottom 30 of the wash chamber and of which the greater part lies under this bottom. Of course, the treatment appliance also has other components, not described in detail here, e.g. a spray arm 29 arranged in the upper area of the wash chamber 17 and used for treating the outside of the endoscope lying in the receiving basket 14. Delivery pumps, heating devices and tanks for treatment additives are also arranged in the appliance.

FIGS. 5 to 7 show a few other details of the measuring unit 9. The measuring unit is secured on the bottom of the wash chamber with the aid of a securing flange 23. The whole measuring unit is composed of a total of eight individual measurement cells 21, each one of which forms its own channel system, and which are arranged uniformly in a circle shape about a central axis 12. Parallel riser pipes 16 protrude from the circular flange 23 and are closed off by the attachment head 10. The lifting movement for docking the attachment head 10 onto the respective attachment adapter is effected with the aid of a lifting device 13 arranged in the lower area. The central supply to all the channel systems is effected via a common distributor chamber 11, which is arranged under the measurement cells 21.

Other details of the measuring unit and of the channel system formed by it, and of an individual measurement cell, will become clear from FIGS. 8 to 10. FIG. 8 again shows the overall arrangement of the individual measurement cells 21 of the measuring unit 9. The treatment fluids, namely air and water, are delivered via an attachment nozzle 22 of the distributor chamber 11. The movement of the attachment head 10 with the riser pipes 16 is effected via a central lifting spindle 26, which is connected to the lifting device 13 via a gear.

As will be seen in particular from FIG. 9, each individual riser pipe 16 moves in the manner of a telescope in a telescope guide tube 25 and is sealed off by suitable sealing means, e.g. O-rings. On the attachment head 10, the riser pipes 16 each open into a channel attachment 4, which forms the end of a conduit system. This conduit system begins at the distributor chamber 11 or at a fluid attachment 39 with a measurement section 6 of a measurement cell 21 and then extends past an inlet valve 8 and via the telescope guide tube 25 to the riser pipe 16. Details of a measurement cell 21 are shown in FIG. 10.

In the measurement section 6, two thermoelectric sensors 7 and 7' are arranged directly one after the other. The sensors are fixed in a sensor housing 24, which also contains the necessary evaluation electronics for a redundant signal measurement. The upper end of the measurement section 6 opens into a valve seat 31, which is assigned to an inlet valve 8. This inlet valve 8 is arranged directly above the sensor housing 24, as will also be seen from FIG. 8. From the valve seat 31, the conduit system leads to the telescope guide tube 25 which, like the measurement section 6, is designed as a bore in a block of material. The riser pipe 16 is movable in the telescope guide tube 25 in arrow direction a.

In a treatment procedure, the charged receiving basket is inserted into the wash chamber, and the wash chamber door is closed. Each individual channel of the endoscope is attached separately to one of the nozzles of the attachment adapter 15. Sensors check the correct closure position of the wash chamber door, whereupon the process can be started. The attachment head 10 is first of all docked from below onto the attachment adapter 15. When this operating position is reached, the treatment of the endoscope begins, on the one hand by various treatment fluids being conveyed through the channels and, on the other hand, also by external treatment with treatment fluids. A control system designated generally by reference number 32 in FIG. 8 compares the through-flow measured in the respective measurement section 6 with a nominal through-flow stored in the control system for the endoscope that is to be treated. In the event of a discrepancy, a warning signal is generated, which is recorded and, if appropriate, interrupts the process. In this way, even endoscope channels that have accidentally not been attached, or endoscope channels that are completely blocked, can be detected in good time. Of course, the control system is connected to each one of the in total eight measurement cells 21.

The through-flow measured in the individual measurement sections 6 is transmitted by the control system to an independent measurement data recorder 33. The latter compares the through-flow detected by the control system 32 with the corresponding through-flow across the second, redundant sensor 7' in the same measurement section 6. In the event of a discrepancy between the through-flows, a warning message is likewise generated.

The entire measurement system is compatible with wash liquor, disinfectants, normal or desalinated water, and air. The measurement system can therefore undergo the same treatment process as the instruments that are to be treated themselves. Moreover, the measurement system can be exposed to temperatures of up to 93° C., with which thermal disinfection is possible. This thermal disinfection process can take place at regular intervals, for example every twelve hours.

In the diagram according to FIG. 11, a treatment process is shown that lasts slightly more than 40 minutes. A cold prewash and a dosed delivery of cleaning agents takes place during the first five minutes. The temperature is then raised to ca. 45° C. and washing performed for about three minutes. Thereafter, the temperature is raised to ca. 58° C., and washing is again performed for about three minutes. Pumping out then takes place and cold water is admitted with a one-minute intermediate rinse at around 35° C. The agent for the intermediate rinse is then pumped out, and a dosed delivery of disinfectant again takes place. A disinfection is then carried out again for about five minutes at 58° C., followed by pumping out and an intermediate rinse for about one minute. After a total process time of about 32 minutes, heating is performed again and rinsing at 58° C. for about 1.5 minutes, followed by pumping out, condensing and drying.

FIG. 12 shows an alternative embodiment of a two-storey receiving basket 34. Endoscopes can be stored in the latter on two different levels, with a double attachment adapter 35 leading to both levels. The double attachment adapter 35 is also shown, slightly enlarged, in FIG. 13. The double attachment adapter has an upper attachment 35 and a lower attachment 36 which, in FIG. 12, would not be visible in reality. Compared to this, the attachment adapter 15 for only one level is shown again in FIG. 14. As will be seen, the single attachment adapter 15 has a total of eight channel attachments in the outer area and in addition three auxiliary attachments in the centre, whereas the double attachment adapter 35 has on each attachment only four channel attachments and additional auxiliary attachments. The auxiliary attachments are used for drying and for checking for air leaks. With the single attachment adapter 15, an endoscope with a maximum of eight individual channels can be treated, whereas the double attachment adapter 35 can be used to treat on each level only an endoscope with a maximum of four individual channels.

FIG. 15 is a schematic representation of an endoscope 2 on which four separate channels can be rinsed through individually. Accordingly, two such endoscopes can be treated using an appliance having a total of eight channel systems. The attachments to be attached to the attachment adapter are the following: 5*a* for the water channel, 5*b* for the air channel, 5*c* for the biopsy channel, and 5*d* for the suction channel. Channel dividers 38 specially created for the endoscopes ensure that, during the treatment, the air and water channels remain separated from each other. During the treatment, each one of the four channels undergoes exactly the same process in terms of treatment fluid, temperature and through-flow measurement.

The appliances according to the invention can of course be adapted to the specific instruments that are to be treated. This applies in particular to the number and structural arrangement of the channel systems.

The invention claimed is:

1. Device for treating and analysing channels in instruments, particularly in endoscopes the device comprising
   a conduit system for feeding at least one treatment fluid to a channel attachment, to which a channel of the instrument can be attached,
   wherein the conduit system has a fluid attachment, which can be connected to a source of treatment fluid,
   and comprising a measuring device for measuring the flow of the treatment fluid in the conduit system, and thus the permeability of a channel of the instrument that can be attached, wherein
   the conduit system has a measurement section, and
   the measuring device has at least one flow sensor, which is arranged in the measurement section, and
   all the treatment steps can be carried out via the conduit system and in particular via the measurement section with the flow sensor, and
   two flow sensors are arranged one after the other in the measurement section, with which the same flow can be measured redundantly, sequentially across the two flow sensors to provide a corresponding through-flow in the measurement section, and
      wherein several conduit systems are combined to form a measuring unit, wherein each conduit system leads to a channel attachment, and wherein all the channel attachments are arranged on a common attachment head.

2. Device according to claim 1, further comprising delivery means for conveying the treatment fluid through the conduit system and a channel of an instrument that can be attached, wherein the measurement section of the conduit system, in relation to a horizontal plane, extends underneath a plane on which the channel attachment lies, wherein the conduit system is inclined with respect to the horizontal plane in such a way that it can be emptied of a liquid when the delivery means is deactivated.

3. Device according to claim 1, wherein the flow sensor is a thermoelectric sensor.

4. Device according to claim 1, wherein an inlet valve is arranged between the flow sensor and the channel attachment.

5. Device according to claim 1, wherein all the conduit systems can be fed with the treatment fluid via a common distributor chamber.

6. Device according to claim 1, wherein the conduit systems are arranged in a circle shape or star shape around a central axis.

7. Device according to claim 1, wherein the conduit system exclusively comprises rigid tubular conduits or lines.

8. Device according to claim 1, wherein at least four of the conduit systems are arranged in a circle shape or star shape around a central vertical axis.

9. Device for treating and analysing channels in instruments, particularly in endoscopes, the device comprising
   a conduit system for feeding at least one treatment fluid to a channel attachment, to which a channel of the instrument can be attached,
   wherein the conduit system has a fluid attachment, which can be connected to a source of treatment fluid,
   and comprising a measuring device for measuring the flow of the treatment fluid in the conduit system, and thus the permeability of a channel of the instrument that can be attached, wherein
   the conduit system has a measurement section, and
   the measuring device has at least one flow sensor, which is arranged in the measurement section,
   all the treatment steps can be carried out via the conduit system and in particular via the measurement section with the flow sensor, and
   the device further comprising an attachment head that can be lifted away from the measurement section by means of a lifting device, from a rest position to a higher operating position, in which the fluid attachments of the conduit systems can be docked onto an attachment adapter assigned to a receiving basket for the instruments.

10. Device according to claim 9, wherein the connection between the measuring unit and the attachment head is effected via riser pipes, which are movable telescopically in the measuring unit.

\* \* \* \* \*